United States Patent
Nair et al.

(10) Patent No.: US 11,125,754 B2
(45) Date of Patent: Sep. 21, 2021

(54) DETERGENT COMPATIBLE ASSAY FOR PROTEIN ESTIMATION

(71) Applicant: AMRITA VISHWA VIDYAPEETHAM, Kollam (IN)

(72) Inventors: Sobha Vijayan Nair, Kollam (IN); Prakash Chandran Ramachandran Nair, Kollam (IN); Bipin Nair, Redmond, WA (US); Kalyani Ajayan, Kollam (IN)

(73) Assignee: Amrta Vishwa Vidyopeetham

(*) Notice: Subject to any disclaimer, the term of this patent is extended or adjusted under 35 U.S.C. 154(b) by 362 days.

(21) Appl. No.: 16/366,865

(22) Filed: Mar. 27, 2019

(65) Prior Publication Data
US 2019/0219591 A1 Jul. 18, 2019

(51) Int. Cl.
*G01N 33/68* (2006.01)

(52) U.S. Cl.
CPC ..... *G01N 33/6842* (2013.01); *G01N 33/6839* (2013.01)

(58) Field of Classification Search
CPC .......... G01N 33/6842; G01N 33/6839
See application file for complete search history.

(56) References Cited

U.S. PATENT DOCUMENTS

| | | | |
|---|---|---|---|
| 7,553,869 B2 | 6/2009 | Czerney et al. | |
| 7,745,153 B2 | 6/2010 | Mallia et al. | |
| 2009/0197348 A1* | 8/2009 | Mallia | G01N 33/683 436/501 |

FOREIGN PATENT DOCUMENTS

CA 2649835 C 1/2016

OTHER PUBLICATIONS

Antharavally B.S., et al., "Quantitation of Proteins using a Dye-Metal-based Colorimetric Protein Assay," Analytical Biochemistry, Elsevier, Feb. 15, 2009, vol. 385(2), pp. 342-345.

* cited by examiner

*Primary Examiner* — Jennifer Wecker
*Assistant Examiner* — Michael Paul Shimek
(74) *Attorney, Agent, or Firm* — Donald R. Boys; Central Coast Patent Agency LLC

(57) ABSTRACT

The invention discloses a detergent-compatible protein assay method, composition and kit based on bio-conjugation reaction between protein and Meldrum's acid activated furfural. The method includes adding MAF in dimethyl sulfoxide (DMSO) to a protein sample solution. The amine functionalities present on the amino acid residues reacts with the MAF instantaneously at room temperature to yield deep purple colored solutions of the corresponding conjugated proteins. The reagent composition added to protein may be in the range of 90-450 mM. The intensities of purple colored solutions were proportional to the protein concentration captured by spectrophotometric measurements. The assay is sensitive in the range of 0.125-15 mg/mL, is compatible with commonly used detergents and reducing agents in protein solutions and may be employed for estimation of protein samples in the presence of detergents and reducing agents.

10 Claims, 6 Drawing Sheets

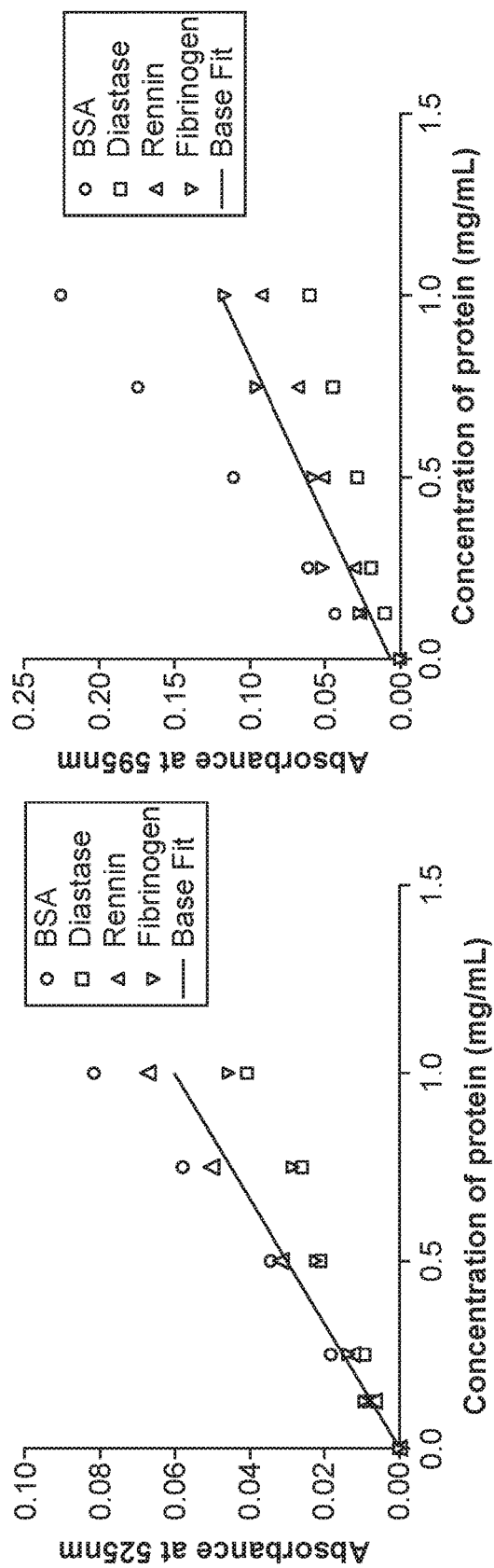
FIG. 4A
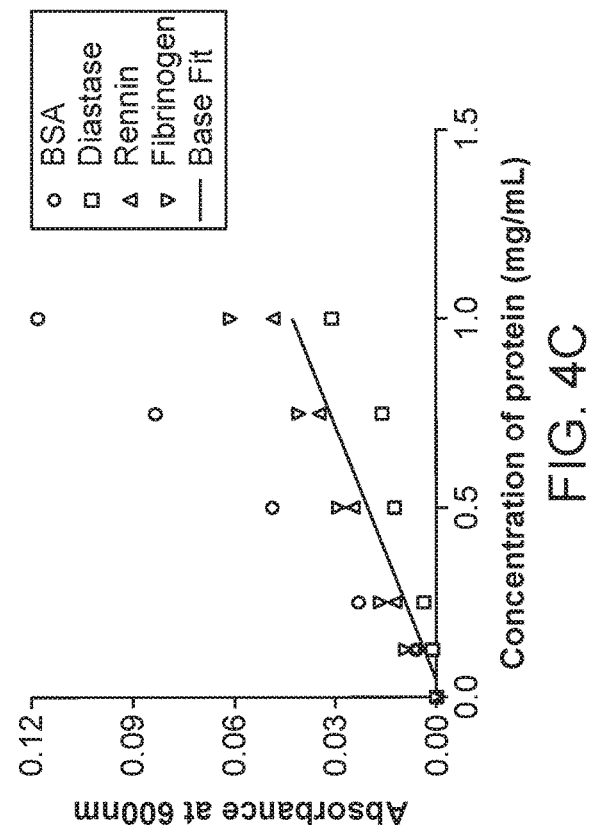
FIG. 4B
FIG. 4C

DETERGENT COMPATIBLE ASSAY FOR PROTEIN ESTIMATION

CROSS-REFERENCES TO RELATED APPLICATIONS

The present application claims priority to Indian Patent Application No. 201841012852 filed on Mar. 12, 2019 entitled "DETERGENT COMPATIBLE ASSAY FOR PROTEIN ESTIMATION", which claims priority to Indian Provisional Patent Application No. 201841012852 entitled "DETERGENT COMPATIBLE ASSAY FOR PROTEIN ESTIMATION" filed on Apr. 4, 2018, both of which are incorporated herein by reference in its entirety.

FIELD OF THE INVENTION

The disclosure relates generally to an assay for proteins and in particular to a method, composition and kit for protein estimation.

DESCRIPTION OF THE RELATED ART

Accurate quantification of protein content is one of the most critical steps in cell biology, molecular biology and other life science research applications. Modern instrumental methods employed for protein quantification including chromatographic and mass spectrometric techniques are expensive and time consuming. Conventional spectrophotometric methods are cheap, fast and the most common way to quantitate protein concentrations. Spectrophotometric assays generally employ UV-visible or fluorescent spectroscopy to determine the concentration of protein, relative to a standard or using an assigned molar extinction coefficient. The common protein assays include the photometric dye-based absorbance measurements, viz. Biuret, Lowry and Bradford assays and fluorescent dye-based assays. However, it may be noted that both the Bradford reagent and Lowry's method are sensitive to detergents like SDS, which are extensively used in protein solubilisation.

A composition, a method, and a kit for a colorimetric protein assay is disclosed in US patent U.S. Pat. No. 7,745,153B2. The Canadian patent CA2649835C discloses reagents, methods and kits for detection of proteins and quantitative determination of protein concentration. Compounds and dye compositions and methods for detecting and quantitating proteins are disclosed in US patent U.S. Pat. No. 7,553,869B2. A dye-metal complex-based total protein determination method is proposed (Antharavally et al., "Quantitation of proteins using a dye-metal-based colorimetric protein assay", Elsevier, 2009, 385, 2; 342-345). The present disclosure both provides an alternative to existing assays and overcomes some of the drawbacks of the existing assays

SUMMARY OF THE INVENTION

The invention in its various embodiments, a detergent-compatible and DMSO-compatible method, composition and kits for detecting protein levels in a sample is included.

In one embodiment, a method of determining protein concentration in a sample is provided. The method includes combining a sample containing proteins with a reagent composition comprising: 90-450 mM of Meldrum's acid activated furfural (MAF) represented by compound of Formula (III), thereby forming a mixture, incubating the mixture for a predetermined time period to form a colored complex, measuring the absorbance of the colored complex, and comparing the absorbance to that of a control sample of known protein concentration to determine the protein concentration of the sample. In some embodiments, the sample contains one or more interfering substances selected from detergents, chelator, sugars, reducing agents, protease inhibitors, lysis buffers, DMSO, Triton X-100, Triton X-114, SDS, Tween 20, Tween 80, Tris buffer, Brij-35, Brij-58, Chaps, Chapso, Deoxycholic acid, Octyl β-glucoside, Nonidet P-40 (NP-40), Octyl β-thioglucopyranoside, NaCl, glucose, PMSF, Lysis buffer, phosphate buffer, HEPES, 2-mercaptoethanol, MOPS, and PBS. In some embodiments, the predetermined time period is in the range of 1 to 360 minutes. In some embodiments, the absorbance for MAF-protein conjugate mixture and the control sample at 525 nm, 600 nm, or both are compared. In some embodiments, the protein sample includes total cellular proteins, membrane proteins, or plasma proteins. In some embodiments, the method has a sensitivity which is greater than or equivalent to Bradford Assay, Biuret Assay or Lowry Assay for the same sample. In some embodiments, the volume to weight fraction of the protein sample to MAF is varied between 0.025 to 0.005. In some embodiments, the concentration of Triton X-100 is in the range of 0.01% to 1%, Tween 20 is in the range of 0.01% to 1%, and SDS is in the range of 0.01% to 0.5%. In some embodiments, the protein sample is a pooled plasma protein or total protein extracted from cells.

In one embodiment, a kit for determining protein concentrations is provided. The kit includes at least a composition comprising Meldrum's acid activated furfural represented by compound of Formula (III) and instructions for determining protein concentration using the kit components This and other aspects are disclosed herein.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 4A shows MAF assay of different proteins at 525 nm.

FIG. 4B shows Bradford assay of different proteins at 595 nm.

FIG. 4C shows MAF assay of different proteins at 600 nm.

DETAILED DESCRIPTION

Figure 1:
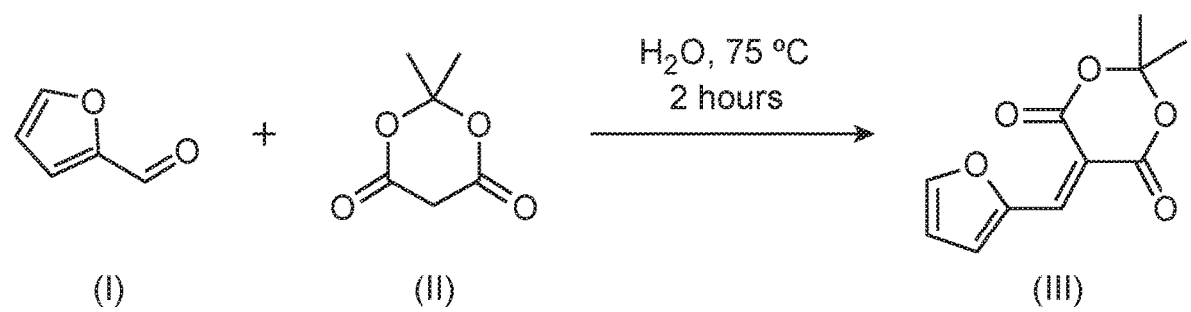
FIG. 1 show synthesis of Meldrum's acid activated furfural (MAF).

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on". Referring to the drawings, like numbers indicate like parts throughout the views. Additionally, a reference to the singular includes a reference to the plural unless otherwise stated or inconsistent with the disclosure herein.

The invention in its various embodiments provides a detergent-compatible and DMSO-compatible method, composition and kits for detecting protein levels in a sample.

In step 101, at least one protein sample is provided for protein detection. The protein sample may be diluted or prepared in any suitable solution such as distilled water or a solution containing one or more additional agents such as detergents, chelator, sugars, reducing agents, protease inhibitors, lysis buffers, DMSO, or the like. The concentration of the protein may vary between 0.01 to 20 mg/mL concentration, typically in the range of 0.125 to 15 mg/mL. In some embodiments, the assay may be conducted in the presence of agents such as Triton X-100, Triton X-114, SDS, Tween 20, Tween 80, Tris buffer, Brij-35, Brij-58, Chaps, Chapso, Deoxycholic acid, Octyl β-glucoside, Nonidet P-40 (NP-40), Octyl β-thioglucopyranoside, NaCl, glucose, PMSF, Lysis buffer, phosphate buffer, HEPES, 2-mercaptoethanol, MOPS, or PBS. In some embodiments, the concentration of Triton X-100 ranges from 0.01% to 1% in the assay volume or 6 to 12% in the sample volume. In some embodiments, the concentration of Tween-20 ranges from 0.01% to 0.8% in the assay volume or 6 to 10% in the sample volume. In some embodiments, the concentration of SDS range from 0.01% to 0.5% in assay volume or 0.1% to 5% in the sample volume. In some embodiments, the concentration of Tris, MOPS, HEPES, or PBS ranges from 0.2 mM to 1.6 mM in assay volume, more typically up to 1.4 mM Tris in the assay volume or 17 mM in the sample, up to 0.24 mM PBS in the assay volume or up to 3 mM in the sample. In some embodiments, the assay is compatible with reducing agent 2-mercaptoethanol at a concentration of up to 1% in assay volume or 12.5% in the sample volume. In some embodiments, the assay is compatible with chelating agent EDTA at a concentration of up to 1 mM in the assay volume or 12.5 mM in the sample volume. In some embodiments, glucose is present up to 12.5 mM in the assay volume or 156 mM in the sample volume. In some embodiments, sucrose is present up to 25 mM in the assay volume or 312 mM in the sample volume.

In some embodiments, the protein sample may be membrane protein preparation, a pooled plasma protein or total protein extracted from cells.

In some embodiments, 0.1-1000 mM MAF is used in the assay, more typically 90-450 mM of MAF.

In step 103, the protein sample is reacted with a Meldrum's acid activated furfural (MAF) in a solvent for a predetermined time period to obtain the Donor Acceptor Stenhouse adduct (DASA) of the corresponding protein.

In some embodiments, the MAF is dissolved in a solvent such as DMSO before adding to protein sample. In various embodiments, the concentration of the MAF may be in the range of 0.01 to 100 mg/mL in the solvent. In some embodiments, the volume to weight fraction of the protein sample to MAF reagent is varied between 0.025 to 0.005. In some embodiments, the weight to weight fraction of the protein sample to MAF reagent is varied between 0.003 to 0.075 by adjusting the stock and reaction volumes. In some embodiments, the predetermined time period is in the range of 1 to 360 minutes, typically about 0.25 h to about 1 h.

In some embodiments, the method involves the bioconjugation of the protein with the MAF to afford the DASA of the protein. In step 105, the conjugate is detected by a spectrophotometric method such as UV-Visible spectroscopy for absorbance measurement. In various embodiments, the absorbance of the protein samples conjugated with the reagent was measured at 450 to 700 nm. In some embodiments, the peak absorbance ($\lambda_{max}$) for MAF is in the range of 400-700 nm, typically 525-600 nm, more typically 525 nm and/or 600 nm.

In some embodiments, the method is suitable for quantification of total cellular proteins, membrane protein preparations or plasma protein samples. In various embodiments, the assay has a sensitivity which is greater than or equivalent to Bradford Assay, Biuret Assay, Lowry Assay, or other assays used in the art.

In various embodiments, a method for determining concentration of proteins present in multiple samples is disclosed. In various embodiments, a method of screening an agent for suitability in the protein assay described above is provided. The method involves incubating protein samples with or without the agent to determine the interference.

Without being bound to any particular theory, it is suggested herein that the chemistry may involve a facile nucleophilic attack at the 5-position of the furan ring of MAF by functionalities on the protein chain, leading to the formation of the corresponding DASAs with a characteristic purple colour. Amine functionalities present on protein, especially the amino acids like tryptophan, arginine and histidine which carry secondary amino groups in their side chains may take part in DASA formation.

While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope.

EXAMPLES

Example 1: Determination of Protein Concentration

Example 1A: Synthesis of Meldrum's Acid Activated Furfural (MAF)

The MAF is prepared by adding Furfural (961 mg, 10 mmol) and Meldrum's acid (1.51 g, 10.5 mmol) sequentially to 30 mL water to produce a homogeneous mixture. Further, this mixture is heated to 75° C. and stirred at that temperature for 2 hours. The reaction was monitored by TLC and was cooled to room temperature on completion to produce a yellow solid. The precipitated yellow solid was collected by vacuum filtration, dissolved in dichloromethane, washed sequentially with 30 mL saturated aqueous $NaHSO_3$, 30 mL $H_2O$, 30 mL saturated aqueous $NaHCO_3$, and 30 mL brine. The organic layer was dried over $MgSO_4$, filtered and the solvent removed by rotary evaporation to give 2.19 g of product as a bright yellow powder. The Mass, NMR and IR spectroscopic data matched the earlier reported values.

Example 1B: Method for Determination of Protein Concentration

The method to determine concentration of proteins in a sample includes synthesis of MAF of formula (III), as shown in FIG. 1. The synthesis involves condensation reaction between furfural of formula (I) and cyclic 1,3-dicarbonyl compounds like Meldrum's acid(2,2-dimethyl-1,3-dioxane-4,6-dione) of formula (II) to yield MAF of formula (III). MAF may undergo a facile ring-opening at room temperature with a wide variety of secondary amine functionalities. The secondary amine functionalities present on the amino acids like tryptophan, arginine and histidine reacts with the MAF instantaneously at room temperature to yield deep purple colored solutions of the corresponding DASA conjugated proteins. The reaction may involve a facile nucleophilic attack at the 5-position of the furan ring of MAF by functionalities on the protein chain to form corresponding DASA. The intensities of purple colored solutions were proportional to the protein concentration. Further, spectrophotometric investigations conducted on protein samples facilitate the development of the assay to determine the exact concentration of proteins present in the various samples.

The concentration dependent absorbance of these conjugated proteins facilitates their quantification by spectrophotometric methods.

Example 2: UV-Visible Spectroscopy

Figure 2:
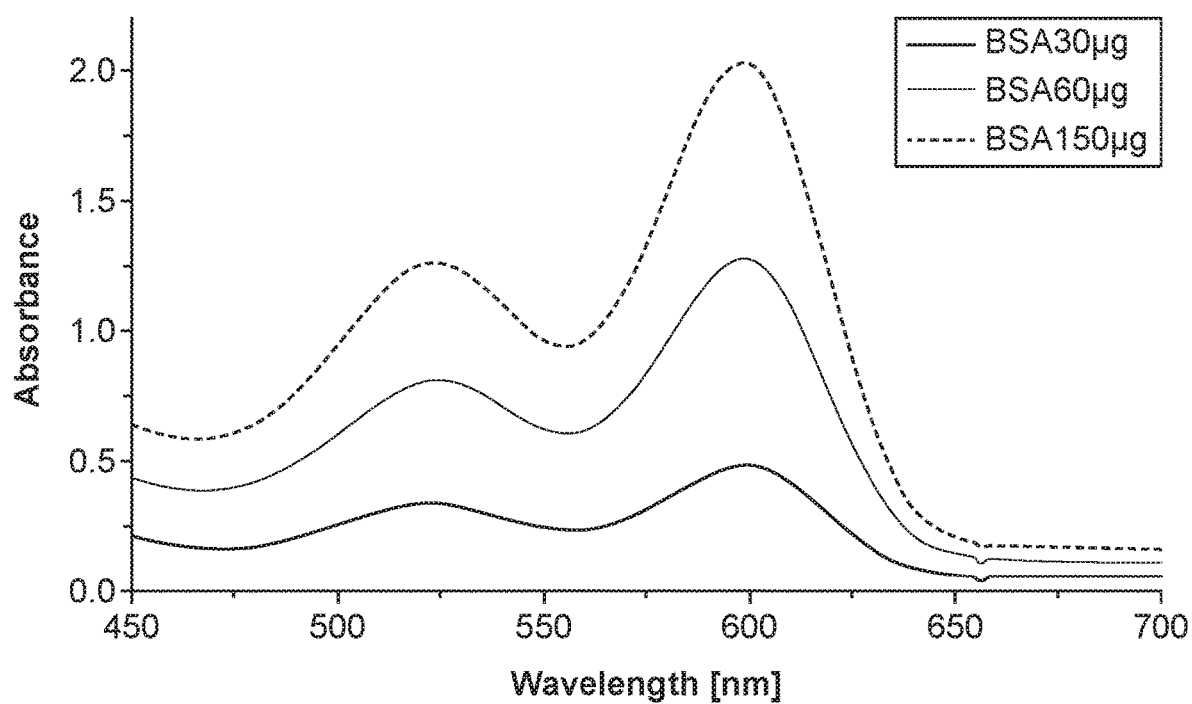
FIG. 2 illustrates the UV-Vis spectrum showing the effect of protein concentration on absorbance.

MAF dissolved in DMSO was added to various concentrations of protein [BSA] solutions at room temperature and UV-Vis spectra were monitored at various intervals of time. The effect of protein concentration on absorbance was investigated by varying the protein concentration while keeping the MAF concentration constant. UV-Vis spectra were recorded after incubation of various protein concentrations with the MAF for 30 minutes as shown in FIG. 2. The purple colored DASA conjugates of proteins exhibited two $\lambda_{max}$ values at 525 nm and 600 nm. It was observed that the absorbance increases with concentration of protein, and this method can be used in protein quantification applications.

Example 3: Standard MAF Protein Assay

An exemplary method for MAF based protein estimation involves dilution of stock standard protein solutions in water. Deionized, double-distilled water (DDW) was used. Proteins were dissolved in DDW. The stock standard protein solutions include 15 mg/mL BSA, Diastase and Rennin. The method involves pipetting 1.5 to 15 mg/mL of protein [10 μL] in a volume of 954, DMSO in microtiter plates. Further, the method involves adding 20 μL of MAF from a stock of 20-100 mg/mL to the wells resulting in a final volume of 125 μL. Appropriate controls for corresponding protein concentration were also pipetted and the reaction mixture was kept for incubation. Colour development proceeds immediately at room temperature. Absorbance at $\lambda_{max}$ 525 and 600 nm were recorded using Microplate Reader [Synergy HT Multimode, BioTek Instruments, and Winooski, Vt.] at time intervals of 15 minutes for one hour. At each incubation absorbance over a range were recorded. The concentration of protein was plotted against corresponding absorbance resulting in a standard curve. The assay was repeated for a lower detection range 0.125-1.5 mg/mL.

Example 4: Assay Development

Example 4A: Determination of Optimum Wavelength Range for Assay

Figure 3A:
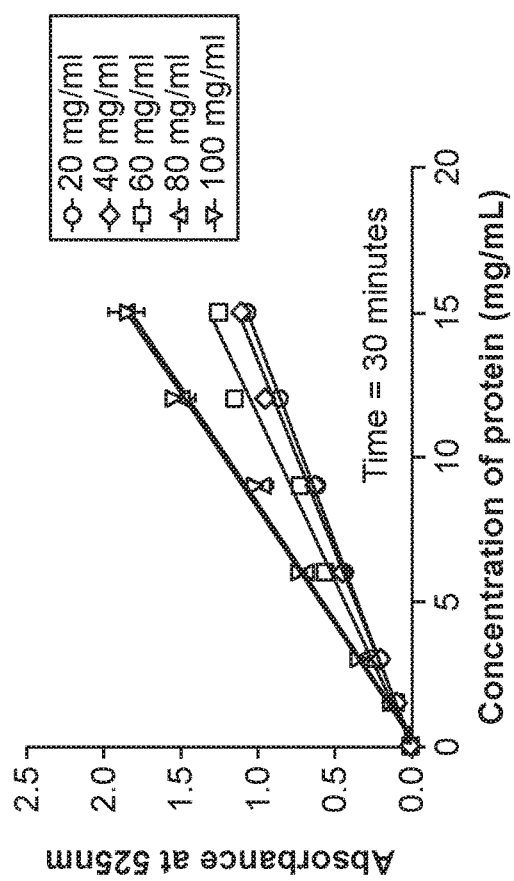
FIG. 3A shows correlation of absorbance with concentration of standard protein sample (BSA) at 525 nm and 600 nm.
Figure 3B:
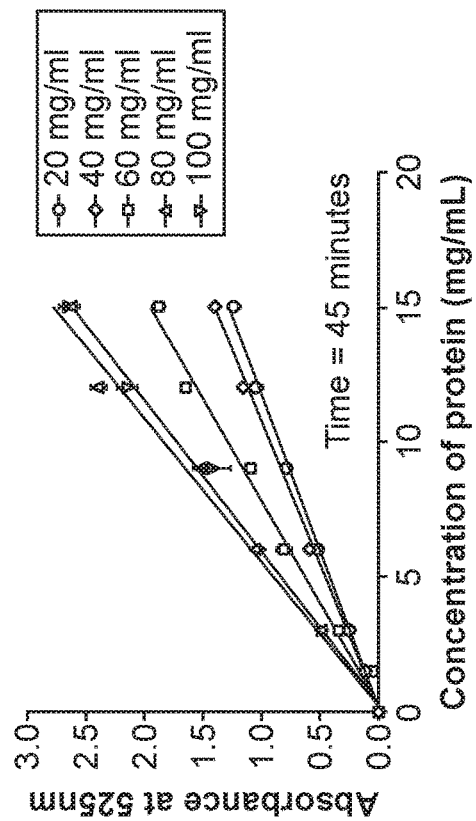
FIG. 3B illustrates correlation of absorbance at 525 nm with concentration of BSA at varying MAF concentration for a time period of 30 minutes.
Figure 3C:
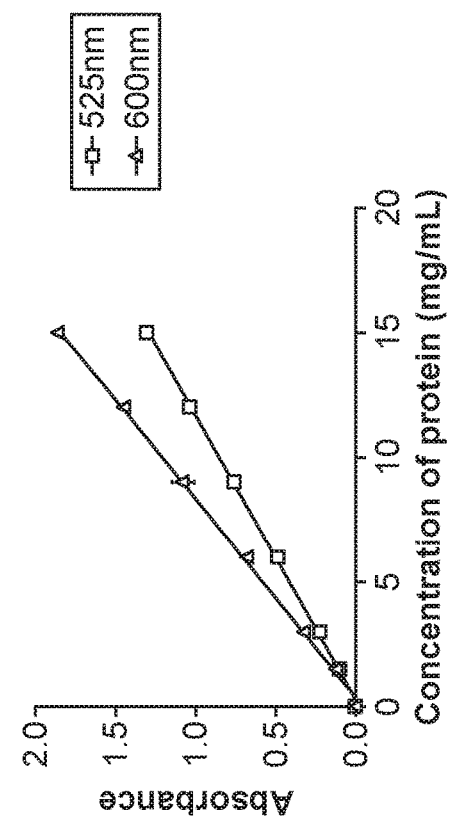
FIG. 3C illustrates correlation of absorbance at 600 nm with concentration of BSA at varying MAF concentration for a time period of 30 minutes.
Figure 3D:
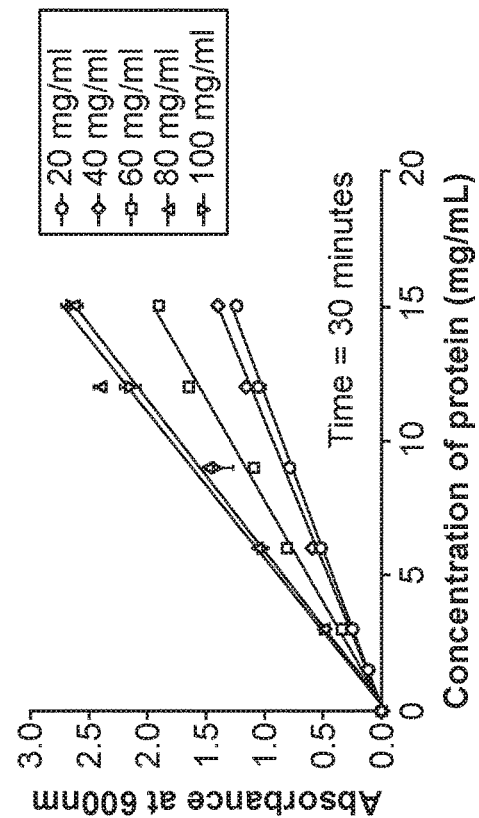
FIG. 3D illustrates correlation of absorbance with concentration of BSA at varying MAF concentration for a time period of 45 minutes at 525 nm.
Figure 3E:
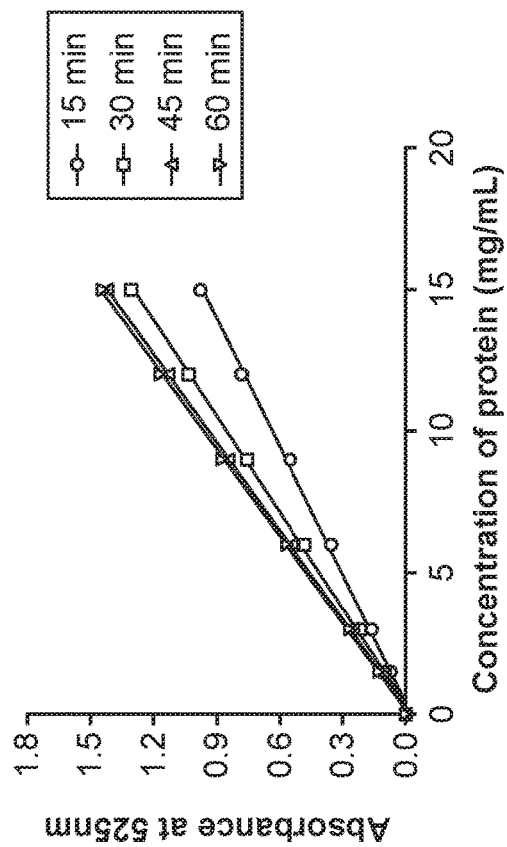
FIG. 3E illustrates correlation of absorbance with concentration of BSA at varying MAF concentration for a time period of 45 minutes at 600 nm.

The assay was performed as before and absorbance values were compared at both 525 and 600 nm. FIG. 3A shows the linearity of the assay for the protein concentration at either 525 or 600 nm with a regression value of 0.99 at both wavelengths. For further studies, both wavelengths were utilized.

Example 4B: Determination of Optimum Concentration Range for Assay

The assay was performed as before and absorbance values were recorded at 525 and 600 nm after 30 minutes or 45 minutes assay time. FIG. 3B-3E represent the standard curves obtained at 525 nm and 600 nm, respectively, for varying MAF concentrations ranging from 20 to 100 mg/ml with protein [BSA] concentration ranging from 1.5 to 15 mg/mL at 30 and 45 minutes with a regression value of 0.99 at both wavelengths. The color formation was proportional to the concentration of the protein whereas its intensity increased with time.

Example 4C: Determination of Optimum Time Range for Assay

Figure 3F:
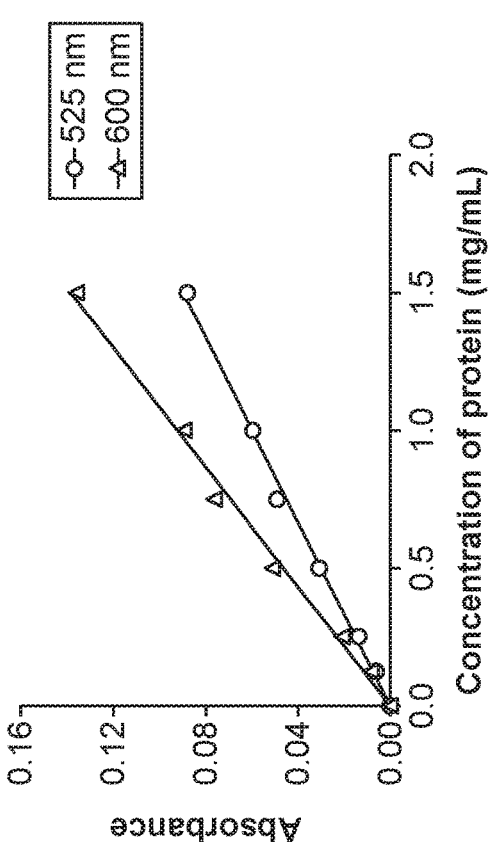
FIG. 3F shows BSA (1.5 to 15 mg/mL) standard curves at 525 nm obtained at different incubation times.
Figure 3G:
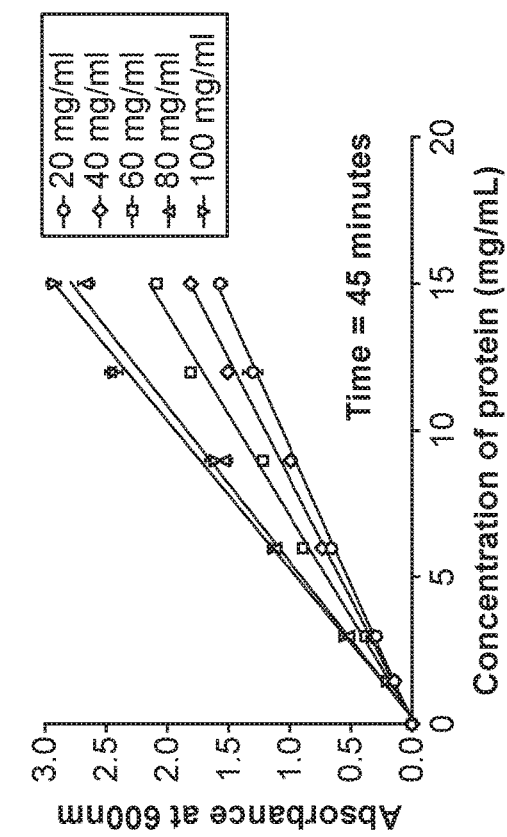
FIG. 3G shows BSA (1.5 to 15 mg/mL) standard curves at 600 nm obtained at different incubation times.
Figure 3H:
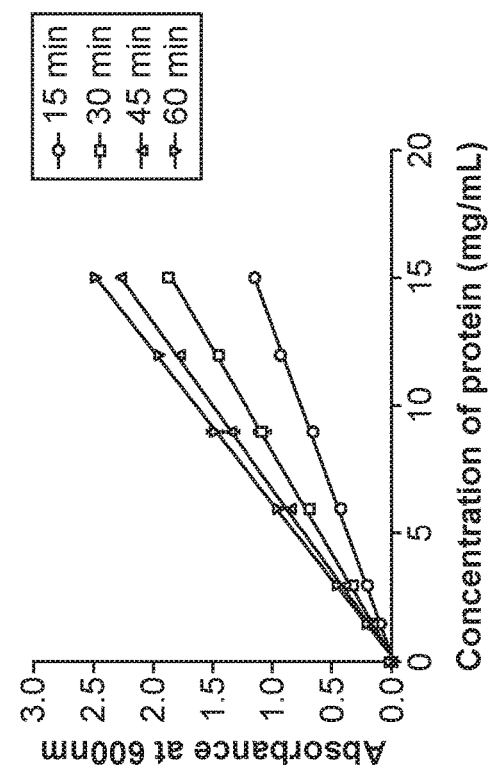
FIG. 3H shows assay sensitivity for 0.125-1.5 mg/mL protein.

The assay was performed as before with 60 mg/ml of MAF and the absorbance was recorded at 525 or 600 nm at 15, 30, 45 or 60 min assay time. For optimizing the time, absorbance values were measured at 15 minute intervals with 60 mg/ml MAF concentrations as shown in FIG. 3F-3G with a regression value of 0.99 at both wavelengths. Further, the assay was found to be sensitive for even lower protein concentrations. FIG. 3H illustrates sensitivity for a concentration range of 0.125-1.5 mg/mL protein concentrations. The assay was found to be stable between 15 minutes to 1 hour. Based on the spectral observations, 30-60 minutes were chosen as optimum incubation time.

Example 5: Protein Assay of Different Proteins

Figure 5A:
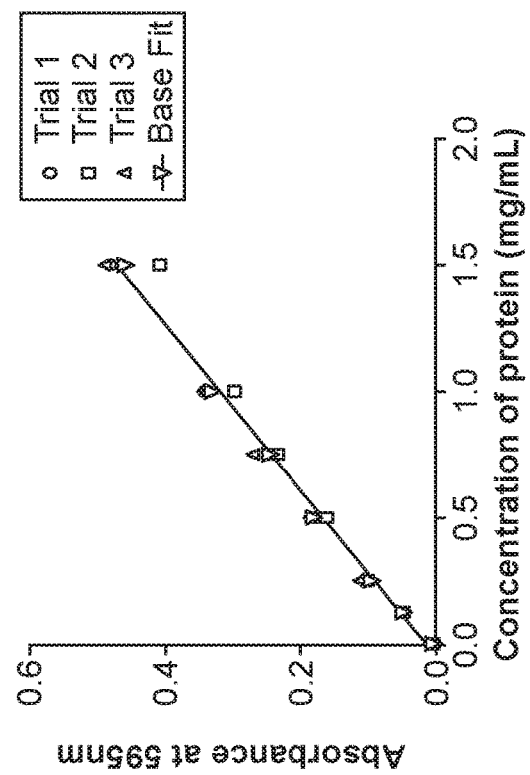
FIG. 5A shows accuracy of results obtained for MAF assay from 3 experiments at 525 nm.
Figure 5B:
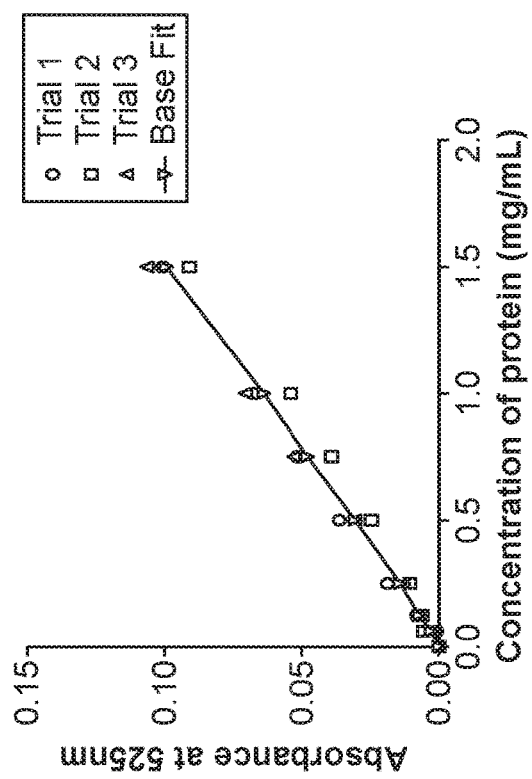
FIG. 5B shows accuracy of results obtained for Bradford assay from 3 experiments at 595 nm.
Figure 5C:
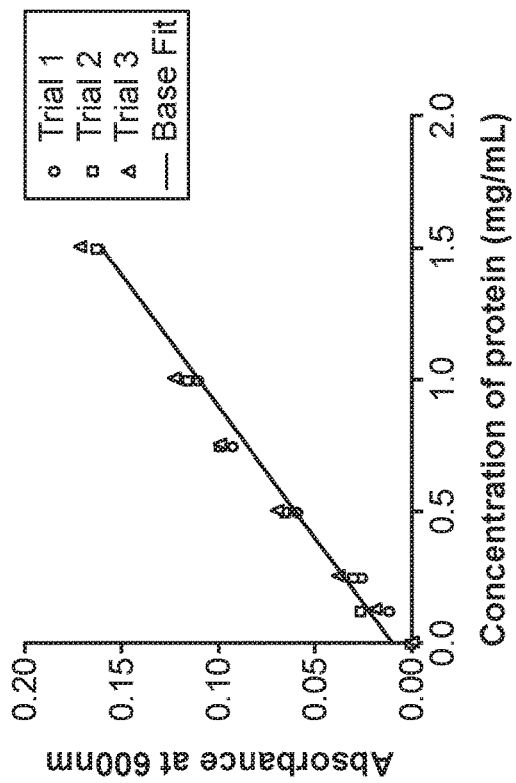
FIG. 5C shows accuracy of results obtained for MAF assay from 3 experiments at 600 nm

The protocol was tested for three more proteins, rennin, fibrinogen and diastase and compared with BSA results. As evident from the plot shown in FIGS. 4A and 4C, all the three additional proteins studied depicted standard graphs with $r^2$ values in the range of 0.99 which suggests that assay is applicable to different proteins. This was comparable to results obtained from Bradford Assay, as show in FIG. 4B. Further, as shown in FIGS. 5A and 5C, the assay reliably produced absorbance values measured at 525 nm and 600 nm from multiple trials which was comparable to Bradford assay measured at 595 nm, as shown in FIG. 5B.

Example 6: Compatibility Studies in the Presence of Reagents

Preliminary studies were conducted to investigate the interference of common reagents used in protein quantification. It was observed that the assay worked well in the presence of detergents like Triton X-100 [1%], SDS [0.5%], Tween 20 [0.8%]. The MAF with the interfering agents for the above-mentioned concentrations reported no change in the absorbance compared to the control [MAF+10 μL water and DMSO]. Keeping the protein concentration same, absorbance was measured in the presence and absence of detergents and compared with Bradford assay. The observations are tabulated in Table 1. The results indicated that presence of Triton X-100[1%] Tween 20 [0.8%] and SDS [0.5%] showed comparable absorbance in the presence of these detergents suggesting the compatibility of DASA assay towards detergents.

Since MAF reacts with nucleophiles, assays involving common buffers like Tris and phosphate are expected to be problematic. However, we observed that by placing a proper control, the estimated amount of protein in the absence and presence of these agents were comparable. It is observed that the MAF assay works well with 1.4 mmM Tris and Phosphate buffer saline [PBS] in the assay volume in the range of pH 7.

Suitability of the assay in the presence of common buffers used for protein extraction and purification, including Tris, Lysis Buffer, HEPES, MOPS phosphate buffer and phosphate buffer saline were assessed. As expected, at high concentrations of the buffers analysed, MAF reacted with the amine functionalities and other nucleophilic centres resulting in absorbance exceeding the upper limit. However, the assay was found to be compatible with the reported concentrations of the buffers (Table 1), where comparable values of estimated protein by setting the proper interference blank. Our observations suggest that the MAF assay works well with protein samples prepared in 17 mM Tris, 18 mM MOPS, 10 mM HEPES, 3 mM Phosphate buffer and 0.25× PBS at neutral pH. A pH of 7-8 was found to be most favourable although others may be utilized as well.

TABLE 1

Protein Quantification In The Presence Of Interfering Agents

| | | | BSA | μg of BSA @ 30 min incubation | |
|---|---|---|---|---|---|
| Maximum tolerable concentration of interfering agents | | | control | Water | Interference |
| | In Stock Solution | In Assay Volume | @30 min | Blank corrected | Blank corrected |
| SDS | 6% | 0.5% | 10.3 | 12 | 10.8 |
| | 2.5% | 0.2% | 10.3 | 11.7 | 10.9 |
| Tween 20 | 10% | 0.8% | 9.3 | 12.6 | 10.1 |
| | 6% | 0.5% | 9.3 | 9.8 | 9.3 |
| Triton X-100 | 12.5% | 1% | 9.8 | 10.9 | 10.1 |
| | 6% | 0.5% | 9.8 | 9.7 | 9.4 |
| NaCl | 250 mM | 20 mM | 9.8 | 9 | 9.1 |
| Glucose | 312 mM | 25 mM | 9.8 | 10.8 | 10.7 |
| | 156 mM | 12.5 mM | 9.8 | 10.2 | 10.1 |
| Sucrose | 312 mM | 25 mM | 9.8 | 10.3 | 10.2 |
| | 156 mM | 12.5 mM | 9.8 | 10.3 | 10 |
| EDTA | 12.5 mM | 1 mM | 9.8 | 11.1 | 10.6 |
| PMSF | 12.5 mM | 1 mM | 9.8 | 9.6 | 10 |
| | 6 mM | 0.5 mM | 9.8 | 9.2 | 9.6 |
| Lysis Buffer | SDS 0.25%, Tris 5.75 mM, Glycerol 0.937% | SDS 0.02%, Tris 0.46 mM, Glycerol 0.075% | 9.8 | 10 | 9.8 |
| Phosphate Buffer | 3 mM | 0.24 mM | 9.8 | 12 | 10.9 |
| 0.25X PBS | 1.25 mM PB, 3.4 mM NaCl | 0.1 mM PB, 0.275 mM NaCl | 9.8 | 12.6 | 10.7 |
| Tris Buffer (pH 6.8) | 17.6 mM | 1.4 mM | 9.8 | 9.7 | 10.6 |
| MOPS | 20 mM | 1.6 mM | 9.8 | 9.4 | 9.4 |
| | 18 mM | 1.4 mM | 9.8 | 9.1 | 9.3 |
| HEPES | 100 mM | 0.8 mM | 9.3 | 12 | 10.3 |
| | 8 mM | 0.6 mM | 9.3 | 12 | 10.2 |
| 2-Mercaptoethanol | 12.5% | 1% | 9.3 | 9.6 | 9.4 |
| | 6% | 0.5% | 9.3 | 9.1 | 9.1 |

Example 7: Protein Estimation from Biological Samples

In order to validate the applicability of the assay to real samples, the estimation of few unknown protein samples from different sources were performed. The efficacy of the method was compared with the Bradford, BCA protein assays and nanodrop protein quantitation technique (Table 2). All the assays were performed with same protein samples including pooled plasma protein, *E. Coli* total protein and total protein from A375 melanoma cell line. These results confirmed that the assay was well suited for estimating proteins from biological samples.

TABLE 2

Comparative estimation of proteins from biological samples

| Assay | Plasma Protein (mg/ml) | *E. coli* total protein (mg/ml) | | A375 melanoma cell total protein (mg/ml) |
|---|---|---|---|---|
| | | DGMB | MTCC40 | |
| MAF | 70.4 ± 4.4 | 2.4 ± 0.4 | 2.1 ± 0.3 | 5.95 ± 0.25 |
| Bradford | 78.5 ± 4 | 1.5 ± 0.4 | 2.2 ± 0.8 | 8 ± 0.6 |
| Nanodrop | 74.2 ± 0.6 | 1.8 ± 0.4 | 3.3 ± 0.3 | 4.7 ± 0.04 |

An efficient assay was established for protein quantitation based on the bio-conjugation of Meldrum's acid Activated Furfural (MAF) to these ubiquitous biomolecules. The assay exploits the bio conjugate chemistry between the proteins and Meldrum's acid Activated Furfural which affords their Donor Acceptor Stenhouse Adducts [DASAs]. The bio-conjugation involves a facile reaction between the amine groups present in the protein with MAF, which affords the corresponding Donor Acceptor Stenhouse Adducts (DA-SAs). These protein derivatives are characterized by their characteristic deep purple colour, which facilitates their quantitation by spectrometric methods.

The detection limit of the MAF assay ranges from 0.125 to 15 mg/mL of proteins and can be followed by reading the absorbance at 525 nm or 600 nm after incubating the protein samples with MAF for a period. Our studies proved that the assay was unaffected by the presence of detergents in the normal experimental range. The fact that the assay was carried out in dimethyl sulfoxide makes it particularly attractive for the quantitation of hydrophobic proteins, which can be solubilised in DMSO and estimated without any interference from the solvent The assay exhibited no interference towards the various detergents and reducing agents like 2-mercaptoethanol. The assay is compatible to chelating agent EDTA as well as sugars like sucrose. The major advantage of the proposed MAF assay lies in the compatibility of the assay towards detergents, reducing and chelating agents. Protein estimation of real samples from various sources which were comparable to the existing protocols, further confirmed the efficacy of the proposed MAF assay.

What is claimed is:

1. A method of determining protein concentration in a sample, the method comprising:
    combining a sample containing proteins with a reagent composition comprising: 90-450 mM of Meldrum's acid activated furfural (MAF) represented by compound of Formula (III):

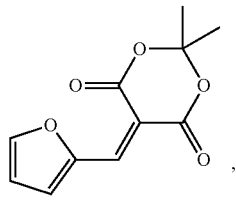

(III)

thereby forming a mixture;
    incubating the mixture for a predetermined time period to form a colored complex;
    measuring the absorbance of the colored complex; and
    comparing the absorbance to that of a control sample of known protein concentration to determine the protein concentration of the sample.

2. The method of claim 1, wherein the sample contains one or more interfering substances selected from detergents, chelator, sugars, reducing agents, protease inhibitors, lysis buffers, DMSO, Triton X-100, Triton X-114, SDS, Tween 20, Tween 80, Tris buffer, Brij-35, Brij-58, Chaps, Chapso, Deoxycholic acid, Octyl β-glucoside, Nonidet P-40 (NP-40), Octyl β-thioglucopyranoside, NaCl, glucose, PMSF, Lysis buffer, phosphate buffer, HEPES, 2-mercaptoethanol, MOPS, and PBS.

3. The method of claim 1, the predetermined time is in the range of 1 to 360 minutes.

4. The method of claim 1, wherein comparing the absorbance comprises:
    comparing absorbance for MAF-protein conjugate mixture and the control sample at 525 nm, 600 nm, or both.

5. The method of claim 1, wherein the protein sample includes total cellular proteins, membrane proteins or plasma proteins.

6. The method of claim 1, wherein the method has a sensitivity which is greater than or equivalent to Bradford Assay, Biuret Assay or Lowry Assay for the same sample.

7. The method of claim 1, the volume to weight fraction of the protein sample to MAF is varied between 0.025 to 0.005.

8. The method of claim 2, wherein the concentration of:
    Triton X-100 is in the range of 0.01% to 1% in the assay;
    Tween 20 is in the range of 0.01% to 0.8% in the assay; and
    SDS is in the range of 0.01% to 0.5% in the assay.

9. The method of claim 1, wherein the protein sample is a pooled plasma protein or total protein extracted from cells.

10. A kit for determining protein concentrations, the kit comprising
    a reagent composition comprising: Meldrum's acid activated furfural represented by compound of Formula (III):

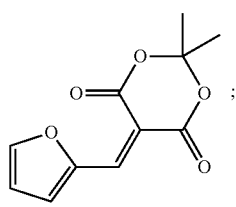

(III)

and
  instructions for determining protein concentration using the kit components.

\* \* \* \* \*

UNITED STATES PATENT AND TRADEMARK OFFICE
CERTIFICATE OF CORRECTION

PATENT NO. : 11,125,754 B2  
APPLICATION NO. : 16/366865  
DATED : September 21, 2021  
INVENTOR(S) : Sobha Vijayan Nair et al.

Page 1 of 1

It is certified that error appears in the above-identified patent and that said Letters Patent is hereby corrected as shown below:

On the Title Page

Assignee now reads: Amrta Vishwa Vidyopeetham  
Assignee should read: Amrita Vishwa Vidyapeetham Signed and Sealed this  
Ninth Day of November, 2021

Drew Hirshfeld  
*Performing the Functions and Duties of the*  
*Under Secretary of Commerce for Intellectual Property and*  
*Director of the United States Patent and Trademark Office*